(12) United States Patent
Goeke et al.

(10) Patent No.: US 8,980,943 B2
(45) Date of Patent: Mar. 17, 2015

(54) 2-OXASPIRO[5.5]UNDEC-8-ENE DERIVATIVES USEFUL IN FRAGRANCE COMPOSITIONS

(75) Inventors: Andreas Goeke, Winterhur (CH); Yue Zou, Shanghai (CN)

(73) Assignee: Givaudan S.A., Vernier (CH)

( * ) Notice: Subject to any disclaimer, the term of this patent is extended or adjusted under 35 U.S.C. 154(b) by 413 days.

(21) Appl. No.: 13/265,937

(22) PCT Filed: Apr. 28, 2010

(86) PCT No.: PCT/EP2010/055711
§ 371 (c)(1), (2), (4) Date: Nov. 1, 2011

(87) PCT Pub. No.: WO2010/125100
PCT Pub. Date: Nov. 4, 2010

(65) Prior Publication Data
US 2012/0058073 A1     Mar. 8, 2012

Related U.S. Application Data

(60) Provisional application No. 61/173,630, filed on Apr. 29, 2009.

(51) Int. Cl.
*A61K 31/335*     (2006.01)
*C07D 311/96*     (2006.01)

(52) U.S. Cl.
CPC .................................. C07D 311/96 (2013.01)
USPC ............................ 514/462; 549/345; 549/331

(58) Field of Classification Search
CPC ............... C07D 307/94; A61K 31/335; A23L 1/22671; C11B 9/0088
USPC .................................... 549/331, 345; 514/462
See application file for complete search history.

(56) References Cited

U.S. PATENT DOCUMENTS

| 4,192,782 A | 3/1980 | Hall et al. |
| 4,524,019 A | 6/1985 | Giersch et al. |
| 7,256,170 B2 | 8/2007 | Vial et al. |
| 2004/0072721 A1 | 4/2004 | Vial et al. |

FOREIGN PATENT DOCUMENTS

EP     1 411 110 A1     4/2004

OTHER PUBLICATIONS

PCT/EP2010/055711—International Search Report, Jun. 29, 2010.
PCT/EP2010/055711—International Written Opinion, Jun. 29, 2010.
GB 0909528.2—Search Report, Sep. 21, 2009.
Zou, Yue, et al., "Organocatalytic Multicomponent α-Methylenation/Diels-Alder Reactions: A Versatile Route to Substituted Cyclohexenecarbaldehyde Derivatives", Chemistry-A European Journal, Jun. 9, 2008, vol. 14, No. 9, pp. 5335-5345.

*Primary Examiner* — Andrew D Kosar
*Assistant Examiner* — Raymond Covington
(74) *Attorney, Agent, or Firm* — Curatolo Sidoti Co., LPA; Joseph G. Curatolo; Salvatore A. Sidoti

(57) ABSTRACT

Disclosed are substituted 2-oxaspiro[5.5]undec-8-ene derivatives of formula (I) and their use as odorants. This disclosure relates furthermore to a method of their production and flavor and fragrance compositions comprising them.

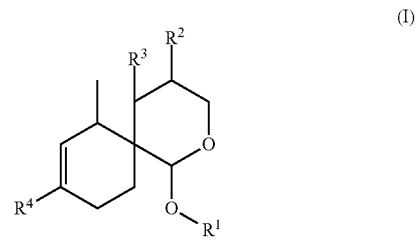

(I)

11 Claims, No Drawings

2-OXASPIRO[5.5]UNDEC-8-ENE DERIVATIVES USEFUL IN FRAGRANCE COMPOSITIONS

CROSS REFERENCE TO RELATED APPLICATIONS

This application is a national stage application of International Application No. PCT/EP2010/055711, filed 28 Apr. 2010, which claims priority from U.S. Patent Application Ser. No. 61/173,630, filed 29 Apr. 2009, from which applications priority is claimed, and which are incorporated herein by reference.

Disclosed are substituted 1-alkoxy-2-oxaspiro[5.5]undec-8-enes and their use as odorants. This disclosure relates furthermore to a method of their production and flavour and fragrance compositions comprising them.

Conventionally, compounds having grapefruit and cassis characteristics have been selected from sulphur-containing organic compounds, such as Corps Cassis®, Corps Pamplemousse® and 1-p-Menthene-8-thiol (Grapefruit mercaptane), and non-sulphur-containing organic compounds such as Buccoxime®, Theaspiran and Etaspiren®. However, the use of known non-sulphur compounds is expensive and the use of sulphur-containing compounds tend to be unstable in various applications and may cause unpleasant off-odors.

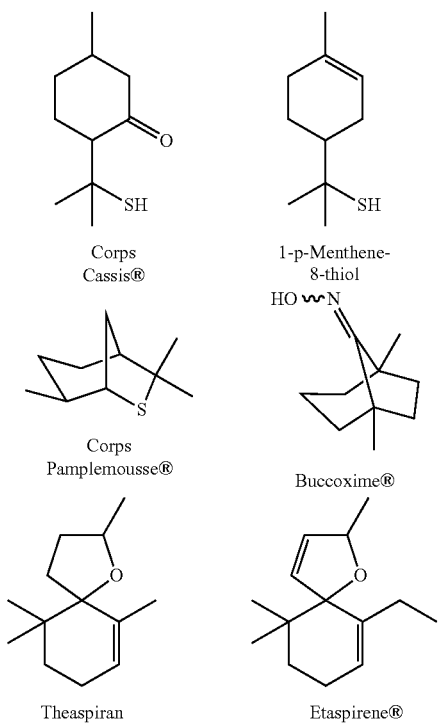

Thus there is still a high demand for new compounds that enhance, modify or improve on odour notes, in particular compounds possessing cassis and grapefruit characteristics.

It has now surprisingly been found that 1-alkoxy-2-oxaspiro[5.5]undec-8-enes constitute new grapefruit and cassis odorants which do not posses the disadvantages of the prior art compounds and thus are valuable new ingredients for the flavour and fragrance industry.

Accordingly, in a first aspect there is provided the use as fragrance or flavour of a compound of formula (I)

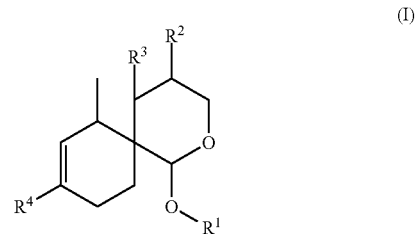

wherein $R^1$ is at least one selected from the group consisting of $C_1$-$C_3$ alkyl (methyl, ethyl, propyl, isopropyl) and $C_2$-$C_3$ alkenyl (vinyl, allyl, propenyl, 1-methyl vinyl);

$R^2$, $R^3$, and $R^4$ are independently selected from hydrogen and methyl.

The compounds of formula (I) comprise one or several chiral centers and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

In particular embodiments, compounds of formula (I) are selected from the group consisting of 1-methoxy-7,9-dimethyl-2-oxaspiro[5.5]undec-8-ene; 1-methoxy-7-methyl-2-oxaspiro[5.5]undec-8-ene; 1-methoxy-5,7-dimethyl-2-oxaspiro[5.5]undec-8-ene; and 1-methoxy-5,7,9-trimethyl-2-oxaspiro[5.5]undec-8-ene.

The compounds of formula (I) may be used alone, as mixtures thereof, or in combination with a base material. As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, "fragrance composition" means any composition comprising at least one compound of formula (I) and a base material, e.g. a diluent conventionally used in conjunction with odorants, such as dipropyleneglycol (DPG), isopropylmyristate (IPM), triethylcitrate (TEC) or alcohol (e.g. ethanol).

The following list comprises examples of known odorant molecules, which may be combined with the compounds of formula (I):

essential oils and extracts, e.g. tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™, eugenol, farnesol, geraniol, Super Muguet™, linalool, menthol, nerol, phenylethyl alcohol, rhodinol, Sandalore™, terpineol or Timberol™;

aldehydes and ketones, e.g. anisaldehyde, α-amylcinnamaldehyde, Georgywood™ hydroxycitronellal, Iso E® Super, Isoraldeine®, Hedione®, Lilial®, maltol, Methyl cedryl ketone, methylionone, verbenone or vanillin;

ethers and acetals, e.g. Ambrox™, geranyl methyl ether, rose oxide or Spirambrene™;

esters and lactones, e.g. benzyl acetate, Cedryl acetate, γ-decalactone, Helvetolide®, γ-undecalactone or Vetivenyl acetate;

macrocycles, e.g. Ambrettolide, Ethylene brassylate or Exaltolide®;

heterocycles, e.g. isobutylquinoline.

The compounds according to formula (I) may be used in a broad range of fragrance applications (product formulations), e.g. in any field of fine and functional perfumery, such as perfumes, air care products, household products, laundry products, body care products and cosmetics. The compounds can be employed in widely varying amounts, depending upon the specific application and on the nature and quantity of other odourant ingredients. The proportion is typically from 0.001 to 25 weight percent of the application. In one embodiment, compounds of formula (I) may be employed in a fabric softener in an amount of from 0.001 to 5 weight percent. In another embodiment, compounds of formula (I) may be used in fine perfumery in amounts of from 0.01 to 5 weight percent, in other embodiments between 0.01 and 5 weight percent. However, these values are given only by way of example, since the experienced perfumer may also achieve effects or may create novel accords with lower or higher concentrations.

The compounds as described hereinabove may be employed in a consumer product base simply by directly mixing the compound of formula (I), a mixture thereof, or a fragrance composition comprising at least one compound of formula (I), with the consumer product base; or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, additionally is provided a method of manufacturing a fragrance application, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactory acceptable amount of a compound of formula (I), or a mixture thereof, as hereinabove described, the odour notes of a consumer product base will be improved, enhanced or modified.

Thus, a method is furthermore provided for improving, enhancing or modifying a consumer product base by means of the addition thereto of an olfactorily acceptable amount of a compound of formula (I), or a mixture thereof.

Also provided is a fragrance application comprising:
a) as odorant a compound of formula (I), or a mixture thereof; and
b) a consumer product base.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body care products, e.g. shampoo, shower gel; air care products and cosmetics, e.g. deodorant, vanishing creme. This list of products is given by way of illustration and is not to be regarded as being in any way limiting.

To the best of our knowledge none of the compounds falling within the definition of formula (I) are described in the literature and are thus novel in their own right.

Accordingly, in a further aspect there is provided a compound of formula (I)

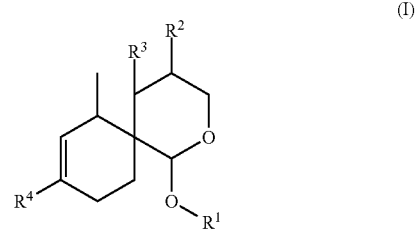

wherein $R^1$ is at least one selected from the group consisting of $C_1$-$C_3$ alkyl (methyl, ethyl, propyl, isopropyl) and $C_2$-$C_3$ alkenyl (vinyl, allyl, propenyl, 1-methyl vinyl); and $R^2$, $R^3$, and $R^4$ are independently selected from hydrogen and methyl.

The compounds of formula (I) may be prepared by reaction of the corresponding halfacetal of formula (II) with the corresponding alcohol $R^1$OH in the presence of a catalytic amount of an acid catalyst under conditions known to the person skilled in the art, as shown in scheme 1 below. The preparation of the halfacetal of formula (II) is describe e.g. by Yue Zou et al. (Chem. Eur. J. 2008, 14, 5335-5345).

Scheme 1:

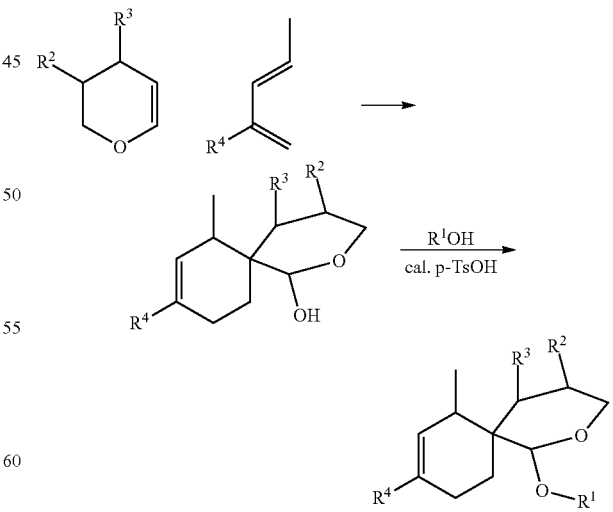

The invention is now further described with reference to the following non-limiting examples. These examples are for the purpose of illustration only and it is understood that variations and modifications can be made by one skilled in the art.

EXAMPLE 1

1-Methoxy-7,9-dimethyl-2-oxaspiro[5.5]undec-8-ene

A solution of 7,9-dimethyl-2-oxaspiro[5.5]undec-8-en-1-ol (5.0 g, 26 mmol) and p-TsOH (50 mg) in methanol (20 ml) was stirred at reflux temperature for 0.5 hours. The mixture was diluted with MTBE, washed with water and brine, dried (MgSO$_4$) and concentrated in vacuo. The residue was distilled bulb-to-bulb to yield a colorless oil (4.3 g, 80%).

$^1$H-NMR (300 MHz, CDCl$_3$): 5.26-5.23 (m, 1H), 4.10 (s, 1H), 3.75-3.52 (m, 2H), 3.35 (s, 3H), 1.97-1.33 (m, 9H), 1.61 (bs, 3H), 0.85 (d, J=7.2 Hz, 3H) ppm. $^{13}$C-NMR (75 MHz, CDCl$_3$): 130.7 (s), 126.3 (d), 103.9 (d), 59.2 (t), 54.5 (q), 37.8 (d), 36.6 (s), 26.5 (t), 25.2 (t), 23.2 (q), 21.6 (2t), 15.6 (q) ppm. GC/MS (EI), endo-isomer (major): 210 (M$^+$, 1), 178 (49), 163 (9), 150 (10), 135 (16), 121 (21), 107 (100), 93 (34), 79 (30), 67 (14), 41 (17).

Odor description: green, fruity, floral, cassis, grapefruit.

EXAMPLE 2

1-Methoxy-7-methyl-2-oxaspiro[5.5]undec-8-ene

The title compound was prepared from 7-methyl-2-oxaspiro[5.5]undec-8-en-1-ol according to the procedure described in Example 1.

$^1$H-NMR (300 MHz, CDCl$_3$): 5.56-5.48 (m, 2H), 4.11 (s, 1H), 3.77-3.52 (m, 2H), 3.36 (s, 3H), 1.98-1.30 (m, 9H), 0.89 (d, J=7.0 Hz, 3H) ppm. $^{13}$C-NMR (75 MHz, CDCl$_3$): 132.0 (s), 123.9 (d), 103.7 (d), 59.2 (t), 54.5 (q), 37.6 (d), 36.8 (s), 25.2 (t), 21.7 (t), 21.5 (t), 21.2 (t), 15.5 (q) ppm. GC/MS (EI), endo-isomer (major): 196 (M$^+$, 4), 164 (33), 149 (2), 136 (7), 121 (17), 108 (36), 93 (100), 79 (31), 67 (8), 41 (11).

Odor description: eucalyptus, fruity, minty, grapefruit, citrus.

EXAMPLE 3

1-Methoxy-5,7,9-trimethyl-2-oxaspiro[5.5]undec-8-ene

The title compound was prepared from 5,7,9-trimethyl-2-oxaspiro[5.5]undec-8-en-1-ol according to the procedure described in Example 1, producing 4 isomers in a ratio of 1:1:1:2.

$^1$H-NMR (300 MHz, CDCl$_3$): 5.31-5.03 (m, 1H), 4.40, 4.35, 4.26, 4.10 (4s, 1H), 3.94-3.73 (m, 1H), 3.58-3.40 (m, 1H), 3.31-3.30 (m, 4H), 2.48-1.17 (m, 10H), 1.11-1.09 (m, 3H), 0.97-0.80 (m, 3H) ppm. $^{13}$C-NMR (75 MHz, CDCl$_3$) major isomer: 131.8 (s), 126.4 (d), 104.5 (d), 56.0 (t), 55.3 (q), 38.7 (s), 34.2 (d), 29.1 (d), 28.3 (d), 28.9 (t), 23.2 (q), 21.7 (t), 17.1 (q), 16.5 (q) ppm. GC/MS (EI): 224 (M$^+$, 6), 192 (68), 177 (16), 136 (26), 121 (79), 107 (100), 93 (34), 79 (14), 67 (16), 55 (15), 41 (14).

Odour description: grapefruit, woody, cassis, pine.

EXAMPLE 4 (COMPARISON)

1-Methoxy-8,9-dimethyl-2-oxaspiro[5.5]undec-8-ene

The title compound was prepared from 8,9-dimethyl-2-oxaspiro[5.5]undec-8-en-1-ol according to the procedure described in Example 1, producing 2 isomers in a ratio of 1:1.

$^1$H-NMR (300 MHz, CDCl$_3$): 4.21, 4.06 (2s, 1H), 3.80-3.50 (m, 2H), 3.36, 3.35 (2s, 3H), 2.29-2.18 (m, 1H), 1.97-1.21 (m, 9H), 1.60, 1.59 (2s, 6H) ppm. $^{13}$C-NMR (75 MHz, CDCl$_3$): 124.8, 123.7, 123.5, 123.3 (2s), 105.4, 102.6 (d), 60.5, 59.6 (t), 55.2, 55.1 (q), 39.5, 39.2 (t), 35.4, 35.2 (s), 30.8, 30.1 (t), 28.2, 28.0, 28.0, 21.3 (2t), 19.3, 19.2 (q), 18.7, 18.6 (q) ppm. GC/MS (EI): 210 (M$^+$, 1), 178 (100), 163 (78), 150 (18), 135 (13), 121 (15), 107 (72), 93 (25), 79 (17), 67 (9), 41 (11).

Odour description: weak, solvent like, camphoraceous.

EXAMPLE 5 (COMPARISON)

1-Methoxy-6,8-dimethyl-2-oxaspiro[4.5]dec-7-ene

The title compound was prepared from 6,8-dimethyl-2-oxaspiro[4.5]dec-7-en-1-ol and methanol according to Example 1, producing 2 isomers in a ratio of 7:3.

$^1$H-NMR (300 MHz, CDCl$_3$), major isomer: 5.43-5.41 (m, 1H), 4.35 (s, 1H), 4.03-3.86 (m, 2H), 3.34 (s, 3H), 2.17-3.14 (m, 7H), 1.63 (s, 3H), 0.98 (d, J=6.8 Hz, 3H) ppm. $^{13}$C-NMR (75 MHz, CDCl$_3$): 131.2 (s), 127.4 (d), 109.5 (d), 66.1 (t), 54.3 (q), 48.2 (s), 35.5 (d), 31.8 (t), 27.2 (t), 23.2 (q), 22.9 (t), 17.8 (q) ppm. GC/MS (EI), endo-isomer (major): 196 (M$^+$, 1), 164 (62), 149 (22), 136 (19), 121 (43), 108 (79), 93 (100), 83 (47), 67 (22), 55 (17), 41 (17).

Odour description: woody, floral, marine

EXAMPLE 6

Fragrance Composition with a Fruity, Crispy Peach and Floral Accord

| | Parts per weight 1/1000 |
|---|---|
| 1-Methoxy-7,9-dimethyl-2-oxaspiro[5.5]undec-8-ene | 20 |
| cis-Hexenyl acetate | 5 |
| Agrumex ™ (2-tert-butyl-cyclohexylacetate) | 200 |
| Hexyl cinnamic aldehyde | 50 |
| Aldehyde C10 (decanal) | 7 |
| Allyl amyl glycolate | 5 |
| Amber core ™ (1-(2-tert-butylcyclohexyloxy)butan-2-ol) | 70 |
| Amyl butyrate | 1 |
| Dimethyl benzyl carbinyl butyrate | 5 |
| Citronellol | 50 |
| Cyclal C (2,4-Dimehtylcyclohex-3-enecarbaldehyde) | 5 |
| Gamma decalactone | 30 |
| Dipropylene glycol | 2.7 |
| Galaxolide 66% in IPM (4,6,6,7,8,8-hexamethyl-1,3,4,6,7,8-hexahydrocyclopenta[g]isochromene) | 100 |
| cis-3-Hexenol | 3 |
| Isopropyl-4-methyl thiazole | 0.3 |
| Linalol | 150 |
| Manzanate ™ (ethyl 2-methylpentanoate) | 25 |
| Ethyl 2-methylbutyrate | 15 |
| Pomarose ™ ((2E)-5,6,7-trimethylocta-2,5-dien-4-one) | 3 |
| Rose oxide | 3 |
| Orange terpenes dist. | 250 |

In this fragrance composition 1-methoxy-7,9-dimethyl-2-oxaspiro[5.5]undec-8-ene (Example 1) boosts the crispy fruitiness of the accord and balances the top and middle notes.

Although the embodiments have been described in detail through the above description and the preceding examples, these examples are for the purpose of illustration only and it is understood that variations and modifications can be made by one skilled in the art without departing from the spirit and the scope of the disclosure. It should be understood that the embodiments described above are not only in the alternative, but to can be combined.

We Claim:
1. A compound of formula (I)

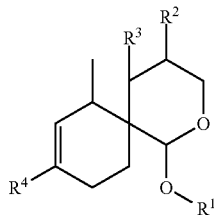

wherein
$R^1$ is at least one selected from the group consisting of $C_1$-$C_3$ alkyl and $C_2$-$C_3$ alkenyl; and,
$R^2$, $R^3$, and $R^4$ are independently selected from hydrogen and methyl.

2. The compound according to claim 1 selected from the group consisting of
1-methoxy-7,9-dimethyl-2-oxaspiro[5.5]undec-8-ene;
1-methoxy-7-methyl-2-oxaspiro[5.5]undec-8-ene;
1-methoxy-5,7-dimethyl-2-oxaspiro[5.5]undec-8-ene; and
1-methoxy-5,7,9-trimethyl-2-oxaspiro[5.5]undec-8-ene.

3. A method of improving, enhancing or modifying a consumer product base by means of addition thereto of an olfactory acceptable amount of a compound of formula (I) as defined in claim 1, or a mixture thereof.

4. A fragrance application comprising as odorant a compound of formula (I) as defined in claim 1, and a consumer product base.

5. The fragrance application according to claim 4 wherein the consumer product base is selected from fine fragrance, household products, laundry products, body care products, cosmetic products and air care products.

6. A fragrance composition comprising a compound of formula (I) as defined in claim 1, or a mixture thereof, and a base material.

7. A fragrance or flavour composition comprising a compound of formula (I) as defined in claim 1 capable of providing a cassis and/or grapefruit note to the composition.

8. The compound according to claim 1 wherein $R^1$ is at least one of methyl, ethyl, propyl, isopropyl, vinyl, allyl, propenyl, or 1-methyl vinyl.

9. A fragrance application comprising as odorant a compound of formula (I) as defined in claim 2, and a consumer product base.

10. The fragrance application according to claim 9 wherein the consumer product base is selected from fine fragrance, household products, laundry products, body care products, cosmetic products and air care products.

11. A method of manufacturing a fragrance application, comprising the incorporation of a compound of formula (I) as defined in claim 1, or a mixture thereof, as a fragrance ingredient, (i) by directly admixing the compound or mixture with a consumer product base, or (ii) by admixing a fragrance composition comprising the compound or mixture which is then mixed with the consumer product base.

* * * * *